US00PP26344P2

(12) United States Plant Patent

Van Der Kolk

(10) Patent No.: US PP26,344 P2
(45) Date of Patent: Jan. 19, 2016

(54) *SALVIA* PLANT NAMED 'CRYSTAL BLUE'

(50) Latin Name: ***Salvia nemorosa* (Linnaeus)**
Varietal Denomination: Crystal Blue

(71) Applicant: Jerry Van Der Kolk, Prairie Grove, IL (US)

(72) Inventor: Jerry Van Der Kolk, Prairie Grove, IL (US)

(73) Assignee: Walters Gardens, Inc., Zeeland, MI (US)

( * ) Notice: Subject to any disclaimer, the term of this patent is extended or adjusted under 35 U.S.C. 154(b) by 139 days.

(21) Appl. No.: 13/999,918

(22) Filed: Apr. 2, 2014

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Annette Para

(57) ABSTRACT

The new and distinct cultivar of perennial *Salvia* plant named 'Crystal Blue' characterized by its large light blue-colored flowers densely arranged in verticils, with compact habit and stiff, upright, branched stems and strong vigorous growth rate and gray-green foliage.

1 Drawing Sheet

Botanical denomination: *Salvia nemorosa* (Linnaeus).
Cultivar designation: 'Crystal Blue'.

BACKGROUND OF THE INVENTION

The present invention relates to a new and distinct cultivar of ornamental Sage plant hereinafter referred to by the cultivar name *Salvia* 'Crystal Blue' or as the new plant. The new plant was discovered on May 19, 2010 in a commercial garden planting of *Salvia* 'May Night' in Lake of the Hills, Ill., USA. The new plant was an isolated whole plant of flowering size. The new *Salvia* was isolated put under further evaluation at a nursery in Zeeland, Mich., USA during the summer of 2012 for the unique traits to be studied. The new plant was then further evaluated and asexually propagated by tip cuttings at the same nursery in Zeeland, Mich. The resulting asexually propagated plants of *Salvia* 'Crystal Blue' have been found to be true to type and stable in successive generations.

SUMMARY OF THE INVENTION

Plants of *Salvia* 'Crystal Blue' have not been observed under all possible environmental conditions. The phenotype may vary somewhat with variations in environment such as temperature, nutrition and light intensity without, however, any variance in genotype.

*Salvia* 'Crystal Blue' can be most closely compared to *Salvia* 'Sal Card 07' U.S. Plant Pat. No. 20,184, *Salvia* 'May Night' (not patented), *Salvia* 'Blue Hill' (not patented) and *Salvia* 'Sensation Sky Blue' (U.S. Plant Patent Pending by another inventor). In comparison to 'Sal Card 07' the new plant is more upright in habit, has lighter blue colored flowers, and the flowers are much larger. In comparison to 'May Night' the new plant is approximately the same size, but is more branched and has larger and lighter blue-colored flowers. In comparison to 'Blue Hill', the new plant is more upright in habit, has thicker diameter stems with more branching, larger flowers but of similar light blue color. Compared to 'Sensation Sky Blue' the flowers are of similar size, but the new plant is larger in stem thickness and in habit, has lighter blue flowers and less reddish pigment in the calyxes.

The following characteristics in combination distinguish *Saliva* 'Crystal Blue' as a new and distinct cultivar:

1. Large light blue-colored flowers densely arranged in verticils;
2. Compact rounded habit and stiff, upright, branched stems;
3. Strong, vigorous and winter-hardy;
4. Rugose gray-green foliage.

BRIEF DESCRIPTION OF THE DRAWINGS

The photographs of the new plant demonstrate the unique traits and the overall appearance of *Salvia* 'Crystal Blue'. The colors are as accurate as reasonably possible with color reproductions. Variation in ambient light spectrum, source and direction may cause the appearance of minor variation in color. The plant used in the photographs was a two-year old plant grown in an open, full-sun trial garden at a wholesale perennial nursery in Zeeland, Mich. with supplemental water and fertilizer when needed. No plant growth regulators have been used.

DETAILED BOTANICAL DESCRIPTION

Figure 1:
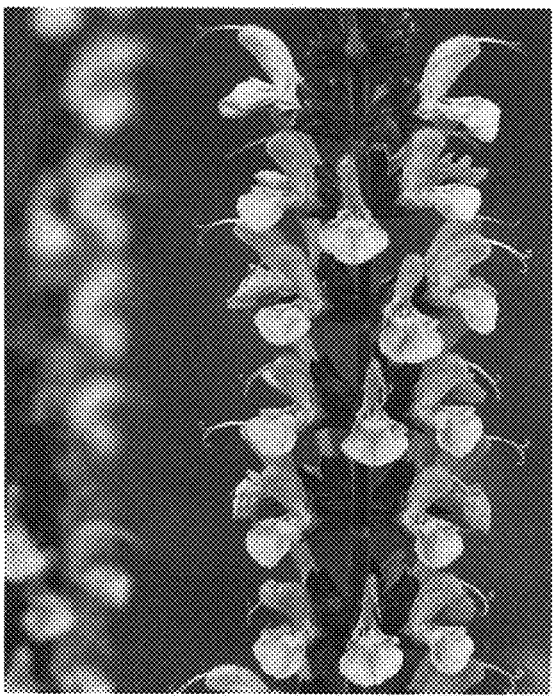
FIG. 1 shows a close-up of the flower scape with the buds and unique light blue petal color.
Figure 2:
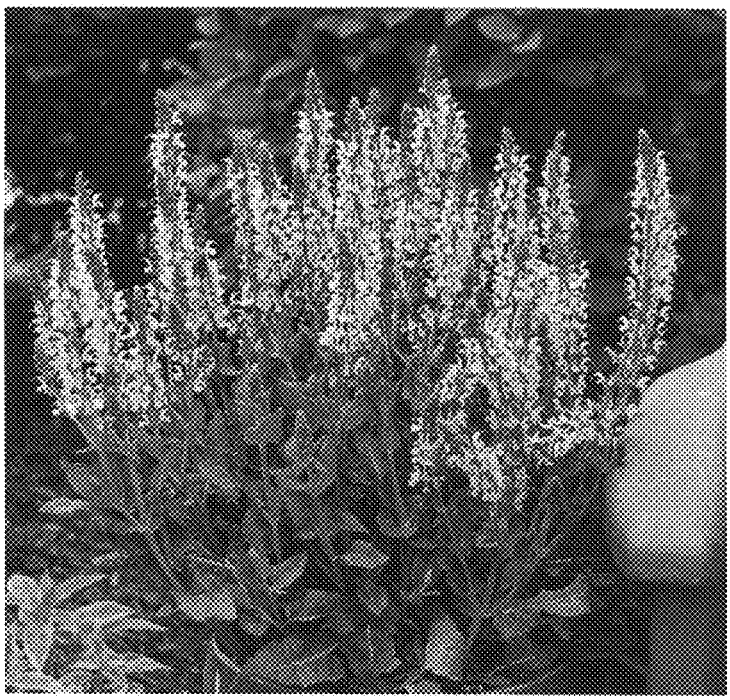
FIG. 2 shows the plant habit in full flower in a landscape.

The following descriptions and color references except where common dictionary terms are used are based on the 2001 edition of The Royal Horticultural Society Colour Chart. *Salvia* 'Crystal Blue' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full-sun trial garden at a wholesale perennial nursery in Zeeland, Mich. Plants were given supplemental water and fertilizer but no plant growth regulators were used.

Botanical classification: *Salvia nemorosa* (Linnaeus).

Parentage: Female or seed parent believed to be *Salvia* 'May Night'; unknown male or pollen parent.

Plant habit: Winter-hardy herbaceous perennial; multi-stemmed, with mostly basal foliage, and flowers in several tightly arranged verticils on branched upright racemes displayed above foliage; in flower with panicles about 55 cm tall and about 60 cm wide at the fullest point; foliage extends up the stems about 30 cm tall and 40 cm wide at base.

Propagation: By herbaceous tip cuttings; time to produce a rooted stems about two weeks.

Growth rate: Rapid, vigorous, finishing in a 65 mm container in about 7 weeks from rooted cutting, and from 65 mm container to flowering 3.8 liter container in about 8 weeks.

Root description: fine, well-branched; color dependent on age and soil type, from cream to dark tan in color.

Foliage: Opposite, simple, rugose, lanceolate; margin crenate, glabrous upper and lower surfaces except veins; acute apex and base cordate to auriculate with lobes sometimes overlapping; lightly pubescent both surfaces; size to about 19.0 cm long; leaf blades about leaves with petiole about 9.0 cm long and 7.0 cm across, decreasing in size distally; average about 12.0 cm long and 3.5 cm across; faint sage fragrance.

Foliage color: Adaxial surface nearest RHS 136B; abaxial surface between RHS N138D and RHS N138C.

Venation: Reticulate; impressed on adaxial side and ridged on abaxial side; pubescent, more heavily on abaxial.

Vein color: Adaxial midrib lighter than RHS 138D, main veins nearest RHS N138C and secondary veins same color as surrounding tissue; abaxial midrib and main veins lighter than RHS 145D and RHS 139D, secondary veins beginning lighter than RHS 145D and RHS 139D and becoming nearest RHS 138D toward leaf margin.

Petiole: Concave adaxial side, convex abaxial side, pubescent; to about 7.0 cm long and 5.0 mm wide, average 4.0 cm long and 3.5 mm wide at base.

Petiole color: Adaxial surfaces center nearest RHS 145D and margins nearest RHS 139C; abaxial center lighter than RHS 145D and RHS 139D and margins between RHS 139B and RHS 139C.

Flower description: Perfect, bilabiate, verticillate with flowering generally beginning at lower verticils and advancing up the scape; average distance between verticils about 9.0 mm, greater proximally and less distally; with lower lip projected at about 90 degree angle to stem and banner petal about 10 degree angle above horizontal; self-cleaning, petals not persistent; flowering beginning late spring for about four weeks and repeating if initial scapes removed.

Flower longevity: About four days on the plant or as cut flower.

Fragrance: Faint sweet honey.

Flower buds one to two days prior to anthesis: Shape is rounded on top and slightly concave below, with rounded apex; pubescent; about 1.0 cm long, 3.5 mm tall and 2.5 mm wide.

Bud color: Petals between RHS N93C and RHS 94B; abaxial calyx distal region nearest RHS 137B, base between RHS144B and RHS 144C, with veins and portions of distal region in more light tinted with nearest RHS 187B; adaxial calyx base nearest RHS 144D, and proximal region between RHS 144B and RHS 144C with darker veins of nearest RHS 137C.

Flowers: About 1.4 cm long, 1.1 cm tall and 6.0 mm wide; clustered at verticils with about six flowers per verticil.

Petals: Bilabiate corolla; upper banner petal and flattened side to side vertically, with notched apex and base fused with labium.

Banner (upper) petal: Minutely pubescent outside, glabrous inside; about 1.3 cm long, 0.8 cm tall and 3.0 mm across.

Labium (lower) petal: Consisting of four lobes, two enrolled proximal lobes about 2.5 mm long and 1.0 mm wide at base with acute apex, two distal lobes about 4.0 mm long 4.0 mm wide with a 1.0 mm apical notch between; lower labium slightly concaved upwards, about 1.2 cm long, 7.0 mm wide at the widest portion and 4.0 mm tall.

Petal color: Upper banner petal between RHS 92C than RHS 97C outside and between RHS 92D and RHS 97D inside; lower labium petal between RHS 97D and RHS 92C in both inner and outer surfaces; fused base inside calyx near white, much lighter than RHS N155A.

Androecium: Two, fused with labium, contained within banner petal except when triggered by pollinator.

*Filament*.—Glabrous, fused about 5.0 mm from base of labium petal; curved around inside of banner petal; about 3.0 mm long and less than 0.5 mm diameter, with flattened flared region at base point of fusion with petal about 1.0 mm across; color proximal region between RHS 85A and RHS 85B, lightening to between RHS 84D and RHS 84C before stamen.

*Anther*.—Glabrous, oblong, less than1.0 mm long and less than 0.5 mm diameter; longitudinal, dorsifixed; color between RHS 160D and RHS 157A.

*Pollen*.—Globose, less than 0.5 mm circumference; color nearest RHS 11B.

Gynoecium: One, curved around inside of banner petal.

*Style*.—About 1.5 cm long and less than 1 mm diameter; color lighter than RHS N155D and RHS 85D at base; darkening distally to between RHS 84B and RHS 85B before stigma split.

*Stigma*.—Split in two and curved in the terminal 2.0 mm; apex pointed; color between RHS 86A and RHS 86B on older flower and on younger flowers nearest RHS 86C.

*Ovary*.—Superior; color nearest RHS 144A.

*Fruit*.—Nutlet, up to four at base inside calyx; rounded, about 1.0 mm diameter; color darker than RHS 200A.

Calyx: Five sepals, three upper and two lower, campanulate, apex acute; fused base; tube about 7.0 mm long and 5.0 mm tall at mouth and 3.0 mm wide; lower set fused to within 3.0 mm of apex and cleft about 3.0 mm deep between upper and lower set; upper set of three fused to closer than 0.5 mm of apex.

Calyx color: Abaxial between RHS 144A and RHS 144B with tinting of between RHS N186C and RHS N187B; adaxial between RHS 144B and RHS N144C with darker veins of RHS 137B.

Bracts: Each verticil subtended by two opposite bracts; apex acuminate, base attenuate, shape nearly cordate; margin minutely pubescent, and glabrous above and below; bract size up to 8.0 mm long and 7.0 mm wide, decreasing distally; color of both surfaces nearest RHS 141B on margin about 1.0 mm wide, with center and base vein nearest RHS 155A.

Peduncles: Quadrangular in cross section, about 16 per plant; strong; mostly upright, up to 60 cm tall and 5.0 mm across; finely pubescent; branches upright at lower nodes with branches to about 15.0 cm long and 3.0 mm across; average internode distance about 6.5 cm.

Peduncle color: Between RHS 138A and RHS 138B in upper and lower regions.

Pedicels: Cylindrical, about 2.0 mm long and 0.5 mm diameter; pubescent; horizontal to about 20 degrees above horizontal.

Pedicel color: Between RHS 146C and RHS 146D.

Disease and pest resistance: Plants of *Salvia* 'Crystal Blue' perform best with adequate moisture and good drainage; are hardy from USDA zone 3 to 8; resistant to diseases and pests beyond that common to *Salvia* has not been noted.

It is claimed:

1. The new and distinct perennial *Salvia* plant named 'Crystal Blue' as herein described and illustrated useful for landscaping as a specimen plant, en masse or as a cut flower.

* * * * *